United States Patent [19]

Commarmond

[11] Patent Number: 5,180,393
[45] Date of Patent: Jan. 19, 1993

[54] ARTIFICIAL LIGAMENT FOR THE SPINE

[75] Inventor: Jacques Commarmond, Saint Remy, France

[73] Assignee: Polyclinique de Bourgogne & Les Hortensiad, France

[21] Appl. No.: 852,556

[22] Filed: Mar. 17, 1992

[51] Int. Cl.⁵ .............................................. A61F 2/08
[52] U.S. Cl. ....................................... 623/13; 623/17; 606/61
[58] Field of Search .................. 623/13, 17; 606/60, 606/61

[56] References Cited

U.S. PATENT DOCUMENTS

| | | | |
|---|---|---|---|
| 3,513,484 | 5/1970 | Hauser | 623/13 |
| 3,988,783 | 11/1976 | Treace | 623/13 |
| 4,743,260 | 10/1988 | Burton | 623/17 |
| 4,834,752 | 5/1989 | Van Kampen | 623/13 |
| 4,946,377 | 8/1990 | Kavach | 623/13 |

FOREIGN PATENT DOCUMENTS 2821678 11/1979 Fed. Rep. of Germany .

Primary Examiner—Ronald Frinks
Attorney, Agent, or Firm—Wall and Roehrig

[57] ABSTRACT

An artificial ligament for the spine is fixed by pedicle screws on two vertebrae of the spinal column and has first and second hollow eyelets, of general diabolo shape, each one including a concave seat intended to receive the head of the fixation screw; a body haivng a narrowed area; a convex hump complementing the concave seat and intended to be directed towards the vertebrae. The artificial ligament itself is made of a flexible textile material having a longitudinal primary winding arranged in figure eight formation between the narrowed areas of two successive eyelets and a transverse secondary winding arranged in contiguous spirals around the primary winding.

5 Claims, 3 Drawing Sheets

1

ARTIFICIAL LIGAMENT FOR THE SPINE

The invention relates to an artificial ligament for the spine, fixed by pedicle screws joining two adjacent vertebrae.

The invention applies particularly to an artificial ligament for the spine, intended to be arranged between each lumbar vertebra, as well as between the last lumbar vertebra and the sacrum, especially the fourth and fifth lumbar vertebrae (L4 and L5) or between the fifth lumbar vertebra and the first sacral vertebra (L5 and S1).

The invention relates more particularly to an artificial ligament for the spine which is of modular design and is intended to be placed consecutively on the lumbar vertebrae, overlapping in the manner of a flight of steps.

This artificial ligament for the spine, intended to be fixed by pedicle screws on two vertebrae of the spinal column, is characterized in that it consists of:
- a first hollow eyelet and a second hollow eyelet, of general diabolo shape, each one comprising in order:
  - a concave seat intended to receive the head of the fixation screw;
  - a body having a narrowed area;
  - a convex hump complementing the concave seat and intended to be directed towards the vertebra;
- an artificial ligament proper, made of a flexible textile material, consisting of:
  - a longitudinal primary winding arranged in figure of eight formation between the narrowed areas of two successive eyelets;
  - a transverse secondary winding arranged in contiguous spirals around the primary winding.

The way in which the invention may be implemented and the advantages which derive therefrom will emerge more clearly from the exemplary embodiment which follows with reference to the attached figures.

Figure 1:
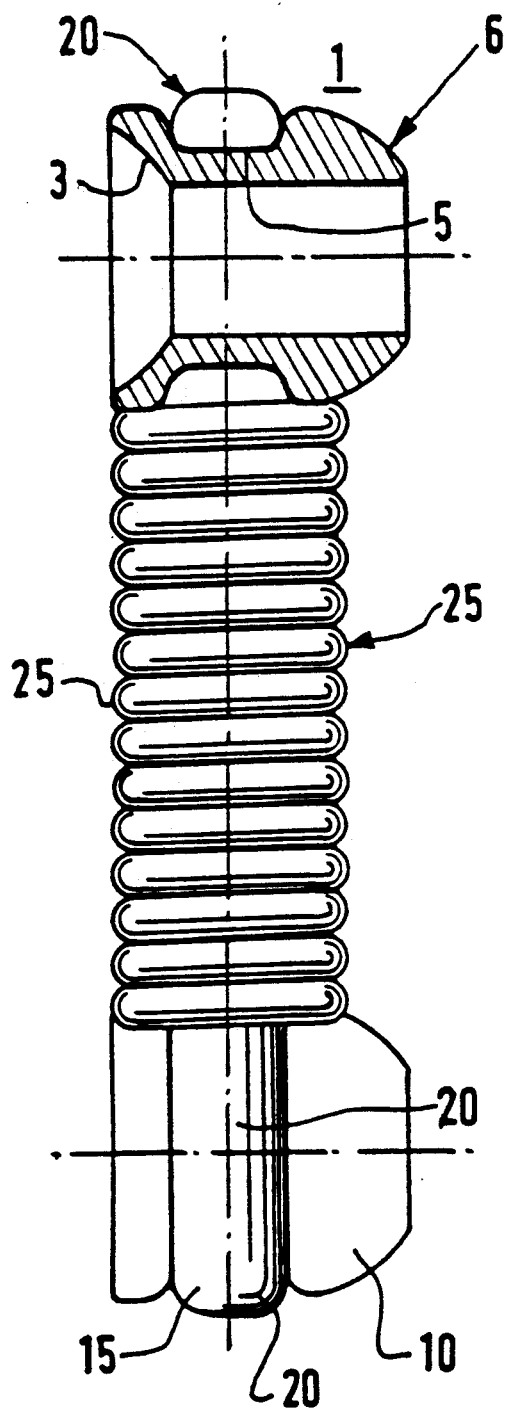
FIGS. 1 and 2 show a cutaway view of an artificial ligament for the spine according to the invention, in a cross-sectional view and front view respectively.
Figure 2:
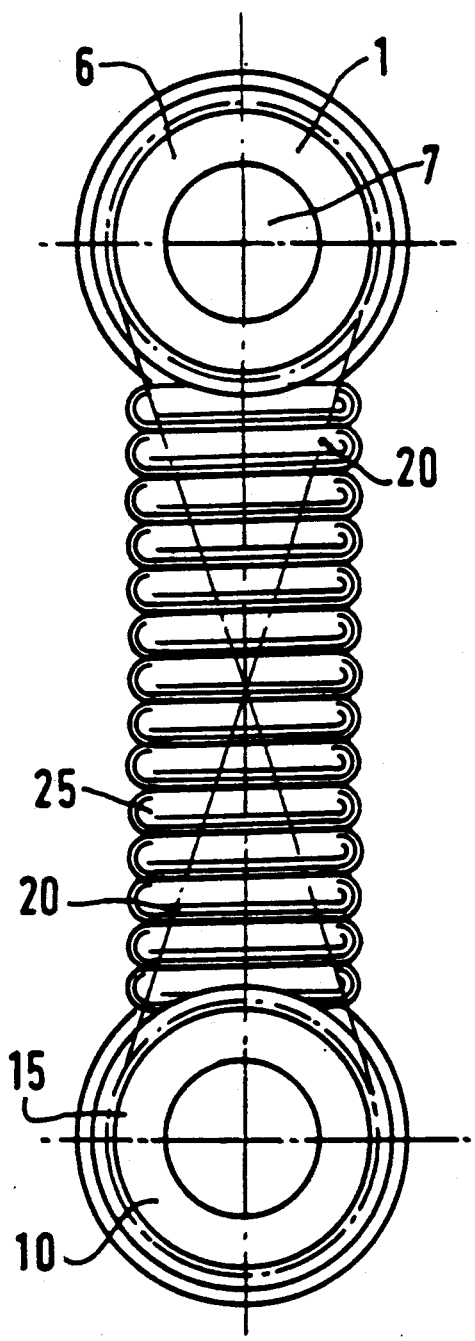
Figure 3:
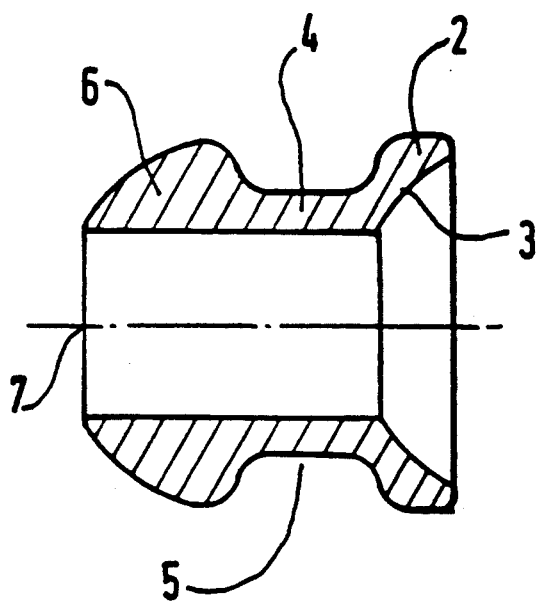
FIGS. 3 and 4 show an eyelet characteristic of the invention, in a cross-sectional view and a front view respectively.
Figure 4:
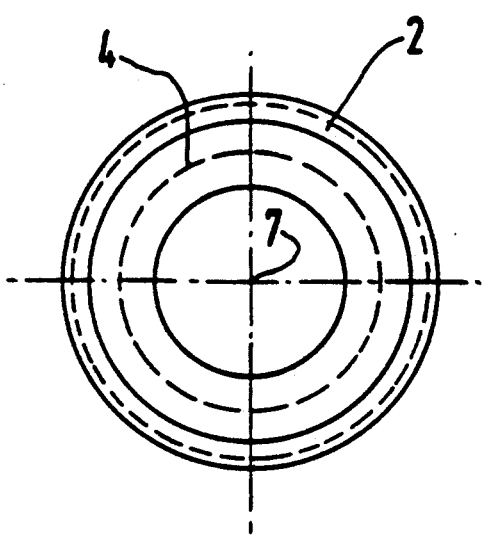

According to the invention (see FIGS. 1-4, the ligament comprises a first hollow eyelet (1) and a second hollow eyelet (10) made of metal (stainless steel, titanium alloy, chromium steel/cobalt), of general diabolo shape. Each of these two eyelets (1, 10) comprises on the outer face (2) a concave seat (3) intended to receive the head of the fixation screw (not shown). This screw, for example of the Muller or Maconnor type, is intended to fix the eyelet on the articular apophyses (see FIG. 5). These cortex screws pass through the pedicles and lodge in the vertebral body. In one variant, this concave seat (3) can receive another consecutive and identical eyelet in such a way as to act as an antishearing ring.

This face (2) is connected to a body (4) in which a central narrowed area (5) is formed, the latter being connected in turn to a convex hump (6) complementing the concave seat (3). As has already been stated, this convex hump (6) is intended to be engaged either in the articular apophysis, a small countersink having been made beforehand therein, in order to act as an antishearing ring, or in the concave seat (3) of a consecutive eyelet (see FIG. 5). A central channel (7) permits the passage of the fixation screw. In order to prevent injuries and to facilitate the articulation of the assembly, the various corners of the eyelet are rounded.

According to another characteristic feature of the invention, the ligament comprises an artificial ligament proper, made of a flexible textile material, consisting of a longitudinal primary winding (20) arranged in figure of eight formation between the narrowed areas (5) and (15) of two successive eyelets (1, 10). This longitudinal primary winding (20) is covered in turn by a transverse secondary winding (25) arranged in contiguous spirals around this longitudinal primary winding (20). The longitudinal primary winding (20) confers rigidity upon the assembly during traction. In contrast, the transverse secondary winding (25) acts as a wedge and gives the ligament stiffness during compression.

In practice, these two windings, the longitudinal primary winding (20) and the transverse secondary winding (25), are formed by a braiding of multifilament yarns of retractable polyester. In this way, by simple drying in a drying stove, the filaments are caused to retract (by 12% for example), which gives the assembly its stiffness and the desired dimension. The cross-section of the braiding constituting the primary winding (20) is preferably smaller than the outer secondary braiding (25) in such a way as to prevent the overlapping of the contiguous spirals of the secondary winding (25).

Figure 5:
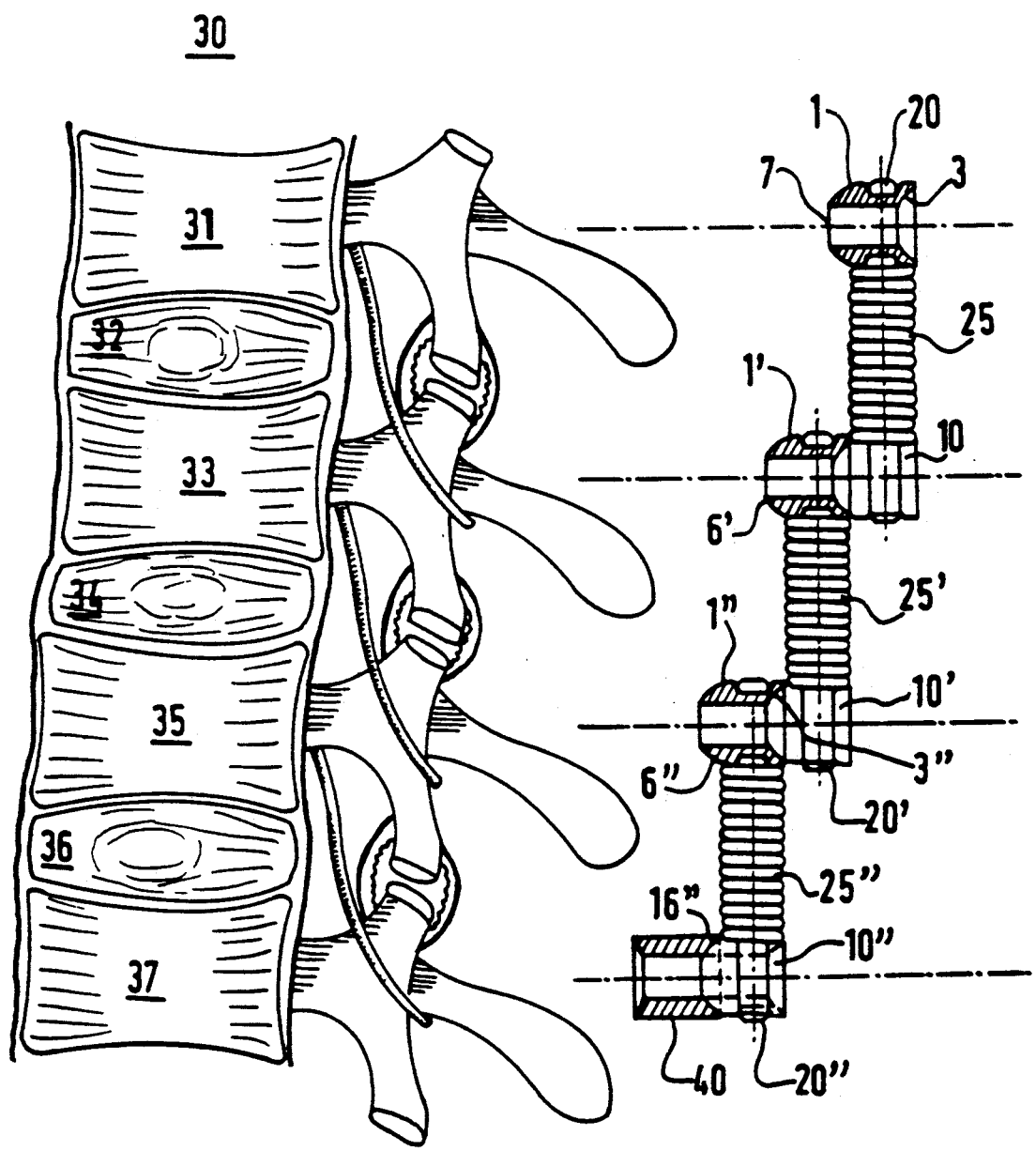
FIG. 5 shows a series of three artificial ligaments for the spine positioned in accordance with the invention.

FIG. 5 shows the way in which the ligament characteristic of the invention can be positioned in order to strengthen the spinal column, designated by the general reference (30), in which the references (31, 33, 35, 37) designate vertebrae, for example (L4, L5 and S1) and the references (32, 34, 36) designate the discs. The first assembly (1, 25, 10) is fixed with the aid of pedicle screws (not shown) on the articular apophyses by passing through the pedicles and lodging in the vertebral body (31, 33). The second assembly (1', 25', 10') strengthens the following vertebrae (33, 35), the bottom eyelet (10) of the first assembly cooperating with the first eyelet (1') of the following assembly, as shown in the figure. Similarly, the third assembly (20", 25", 10") cooperates with the second assembly in order to strengthen the vertebrae (35, 37). It will be understood that the hemispherical male (6) and female (3) parts of the eyelets fit one inside the other in order to constitute a compact assembly permitting an adjustment with a slight swivelling. Similarly, the narrowed area (4), which receives the longitudinal primary winding (20), makes it possible, by virtue of this hourglass shape, to immobilize this primary winding (20) in translation without overloading it, which prevents fatigue ruptures (in the long term during use).

In one variant shown in FIG. 5, the characteristic eyelet can cooperate with a heightening strut (40) of the same dimension and same height as the characteristic eyelet (10").

The stiffness of the ligament according to the invention is appreciable both during traction and during compression.

In a practical embodiment, good results have been obtained with eyelets whose diameter and length are in the region of ten millimetres, pierced with a channel (7) of approximately seven millimetres, and in which the radii of curvature of the concave seat (3) and of the convex hump (6) are equal to five millimetres, which makes it possible to receive Muller screws of 4.5 mm diameter or Maconnor screws of 5 mm. The longitudinal primary winding (20) is formed by sixty figure of eight passages of a high-strength retractable polyester yarn of 1000 denier. This primary winding (20) is then covered with a braiding of contiguous spirals of three millimetres diameter, made from the same high strength retractable polyester yarn of 1000 denier on six spindles, in such a way as to form a secondary winding (25). The outer braiding (25) forming the secondary winding is wound tightly around the inner primary winding (20) in such a way as to close via its ends the loops of the primary winding. Once this assembly has been formed, it is heat-treated in a known manner in order to cause the retraction of the polyester yarns. This gives the assembly the required elasticity during traction with a low amplitude until the opening of the ends of the eight formation of the primary winding which is in effect practically inextensible.

The space between two eyelets (1, 10) of the same assembly is modular, for example twenty-five, thirty, thirty-five millimetres.

Under these conditions, it has been observed that the maximum amplitude between the lengthening of this ligament in kyphosis and its compression in lordosis is approximately two millimetres.

The artificial ligament for the spine according to the invention has a number of advantages compared with the solutions known to date. There may be mentioned:
- the firm implantation in the pedicle, possible after complete laminectomy;
- the flexibility preserving the pedicle fixation combined with a stiffness during traction and during compression, limiting the kyphosis/lordosis between two vertebrae and, consequently, the shearing of the discs;
- the possibility of modular implantations making it possible to extend as desired the number of intervertebral stages to be fixed, the different sizes proposed for each module matching each anatomical situation.

I claim:

1. Artificial ligament (i) for the spine, intended to be fixed by pedicle screws on two vertebrae (31, 33) of the spinal column (30), characterized in that it consists of:
    - a first hollow eyelet (1, 1', 1'') and a second hollow eyelet (10, 10', 10''), of general diabolo shape, each one comprising in order:
    - a concave seat (3) intended to receive the head of the fixation screw;
    - a body (4) having a narrowed area (5); a convex hump (6) complementing the concave seat (3) and intended to be directed towards the vertebra (31–37);
    - an artificial ligament proper, made of a flexible textile material, consisting of:
    - a longitudinal primary winding (20) arranged in figure of eight formation between the narrowed areas (5, 15) of two successive eyelets (1, 10);
    - a transverse secondary winding (25) arranged in contiguous spirals around the primary winding (20).

2. Artificial ligament for the spine according to claim 1, characterized in that the eyelets (1, 10) are made of metal.

3. Artificial ligament for the spine according to claim 1, characterized in that the hollow eyelets (1, 10) are made of metal selected from the group consisting of stainless steel, titanium alloy, chromium steel/cobalt.

4. Artificial ligament for the spine according to claim 1, characterized in that the inner longitudinal primary winding (20) and the outer transverse secondary winding (25) are formed by a braiding of multifilaments of retracted polyester.

5. Artificial ligament for the spine according to claim 1, characterized in that the ligament also comprises a strut (40) which is adapted to bear on one side of the vertebra (37) and on the other side of the convex hump (16'') in the eyelet (10'').

* * * * *

UNITED STATES PATENT AND TRADEMARK OFFICE
CERTIFICATE OF CORRECTION

PATENT NO. : 5,180,393
DATED : January 19, 1993
INVENTOR(S) : Jacques Commarmond It is certified that error appears in the above-indentified patent and that said Letters Patent is hereby corrected as shown below:

On the Title page, item [73], Assignee: should be --Jacques Commarmond and Impact--.

Signed and Sealed this

Fifth Day of April, 1994

Attest:

BRUCE LEHMAN

Attesting Officer      Commissioner of Patents and Trademarks